(12) United States Patent
Lin et al.

(10) Patent No.: US 12,179,004 B2
(45) Date of Patent: Dec. 31, 2024

(54) SAFETY SYRINGE

(71) Applicant: Shanghai Kindly Medical Instruments Co., Ltd., Shanghai (CN)

(72) Inventors: Sen Lin, Shanghai (CN); Dongke Liang, Shanghai (CN); Hongxin Zhou, Shanghai (CN); Lei Li, Shanghai (CN); Peng Lin, Shanghai (CN); Yan Gu, Shanghai (CN)

(73) Assignee: Shanghai Kindly Medical Instruments Co., Ltd., Shanghai (CN)

( * ) Notice: Subject to any disclaimer, the term of this patent is extended or adjusted under 35 U.S.C. 154(b) by 399 days.

(21) Appl. No.: 17/642,177

(22) PCT Filed: Sep. 2, 2021

(86) PCT No.: PCT/CN2021/116135
§ 371 (c)(1),
(2) Date: Mar. 10, 2022

(87) PCT Pub. No.: WO2022/170757
PCT Pub. Date: Aug. 18, 2022

(65) Prior Publication Data
US 2023/0146686 A1    May 11, 2023

(30) Foreign Application Priority Data

Feb. 9, 2021 (CN) .......................... 202110180431.0

(51) Int. Cl.
*A61M 5/32* (2006.01)
(52) U.S. Cl.
CPC .................... *A61M 5/322* (2013.01)
(58) Field of Classification Search
CPC .. A61M 5/322; A61M 5/3234; A61M 5/5066; A61M 5/508; A61M 5/3232;
(Continued)

(56) References Cited

U.S. PATENT DOCUMENTS 4,850,968 A * 7/1989 Romano ............... A61M 5/326
604/218
5,395,346 A    3/1995 Maggioni
(Continued)

FOREIGN PATENT DOCUMENTS

| AU | 3433402 A | 11/2002 |
| CA | 2602135 A1 | 4/2008 |

(Continued)

OTHER PUBLICATIONS

2nd Office Action, CN application 2021101804310, Feb. 15, 2023.
(Continued)

*Primary Examiner* — Chelsea E Stinson
*Assistant Examiner* — Anh Bui
(74) *Attorney, Agent, or Firm* — David R. Stevens; Stevens Law Group

(57) ABSTRACT

Disclosed is a safety syringe that comprises a needle sleeve (1), a needle base (3) and a core rod (2). First claws (34) on the needle base (3) are configured to clamp in a first groove (111) on an inner wall of the needle sleeve (1), one of a proximal end of the needle base (3) and a distal end of the core rod (2) is provided with second claws (33), and the other one thereof is provided with a position-limiting member; the second claws (33) are configured to abut against the position-limiting member along a slanted surface. When the core rod (2) slides towards a distal side to perform injection, the second claws (33) are forced to slide along the slanted surface to pass over the position-limiting member and become hooked onto the position-limiting member, thereby realizing interlocking of the needle base (3) and the core rod (2), and during this process, the core rod (2) slides to drive the first claws (34) to slip out of the first groove (111); or when the core rod (2) retracts, the core rod (2) exerts a pulling force on the needle base (2) towards the proximal (Continued)

side so as to force the first claws (34) to slip out of the first groove (111); the needle base (3) slides towards the proximal side together with the core rod (2), thereby simplifying the structure of the safety syringe.

15 Claims, 10 Drawing Sheets

(58) Field of Classification Search
CPC ............ A61M 5/50; A61M 2005/3231; A61M 2005/3224; A61M 2005/3235; A61M 2005/5033; A61M 2005/5073; A61M 2005/3223; A61M 2005/3261
See application file for complete search history.

(56) References Cited

U.S. PATENT DOCUMENTS

| | | | | |
|---|---|---|---|---|
| 7,285,110 | B2* | 10/2007 | Fitzgerald | A61M 5/322 604/110 |
| 2004/0147876 | A1* | 7/2004 | Maggioni | A61M 5/322 604/110 |
| 2011/0066115 | A1* | 3/2011 | Choi | A61M 5/322 604/197 |

FOREIGN PATENT DOCUMENTS

| | | | |
|---|---|---|---|
| CN | 2710665 | Y | 7/2005 |
| CN | 2750815 | Y | 1/2006 |
| CN | 1803212 | A | 7/2006 |
| CN | 1845767 | | 10/2006 |
| CN | 2845821 | Y | 12/2006 |
| CN | 1943809 | A | 4/2007 |
| CN | 201020108 | Y | 2/2008 |
| CN | 101444649 | | 6/2009 |
| CN | 101513547 | | 8/2009 |
| CN | 201399137 | | 2/2010 |
| CN | 201505347 | | 6/2010 |
| CN | 102488948 | A | 6/2012 |
| CN | 202569091 | | 12/2012 |
| CN | 202654501 | U | 1/2013 |
| CN | 103721320 | | 4/2014 |
| CN | 109350805 | | 2/2019 |
| JP | 1995051372 | A | 7/1994 |
| JP | 1999342200 | | 11/1998 |
| WO | 9107198 | | 5/1991 |
| WO | 2007065324 | | 6/2007 |
| WO | 2011012014 | | 2/2011 |

OTHER PUBLICATIONS

1st Office Action, JP application 2022-515636, mailed May 16, 2023.
Search Report and Written Opinion, PCT/CN2021/116135, Dec. 8, 2021.
1$^{st}$ Office Action of corresponding CN application English translation 2021101804310.
Extended European Search Report EP 21859331 Oct. 17, 2022.

* cited by examiner

SAFETY SYRINGE

TECHNICAL FIELD

The present application belongs to the technical field of medical instruments, and particularly relates to a safety syringe.

BACKGROUND

Injection is an indispensable medical procedure in modern medical care, and syringes are an indispensable type of medical instrument in medical care. If a syringe is repeatedly used instead of being manually destroyed after use, cross infection of patients or users, for example, cross infection due to transmission of certain viruses in blood, may be caused.

Therefore, syringes currently on the market usually adopt safety syringes of the one-time self-destruction type. Wherein, the prior art provides a one-time self-destruction type safety syringe that comprises a needle sleeve, a core rod, a needle base, a needle tube, and a locking ring. Wherein, the needle tube is fixed on a distal end of the needle base, a curved protrusion is provided on an outer wall of a proximal end of the needle base, and a curved groove is provided on an inner wall of the needle sleeve for the curved protrusion to clamp in; a position-limiting groove is provided on a proximal end surface of the needle base, and a groove mouth of the position-limiting groove forms a hooking structure; the locking ring comprises a ring body with multiple elastic detents formed on an inner wall of the ring body and a clamping core formed on a distal end of the ring body, and a distal end of the clamping core is flared outwards to form a clamping hook. The clamping core of the locking ring extends into the position-limiting groove of the needle base; the ring body and the elastic detents are positioned outside a proximal end of the position-limiting groove, and an outer wall of the ring body is closely fitted on the inner wall of the needle sleeve.

Before injection, the clamping hook of the clamping core is spaced apart by a distance from the hooking structure of the needle base; when operating the core rod to perform injection, with a conical frustum provided on a distal end of the core rod, the core rod gradually moves in the needle sleeve in a direction towards the locking ring, until the conical frustum passes through the ring body of the locking ring and becomes hooked onto the elastic detents, so as to complete the injection. After the injection, the entirety of the needle base and the needle tube needs to be pulled into the needle sleeve in order for the subsequent self-destruction of the core rod, and because the conical frustum of the core rod is hooked on the elastic detents, when the core rod moves towards the proximal side, the core rod brings the locking ring to move together towards the proximal side, while the needle base does not move at this time; along with continuous movement of the core rod towards the proximal side, when the clamping hook becomes hooked onto the hooking structure, the needle base and the locking ring become fixed together, and after that, if the core rod continues to move towards the proximal side, it will bring both the locking ring and the needle base to move together towards the proximal side of the needle sleeve, and as a result, the curved protrusion on the outer wall of the needle base slips out of the curved groove on the inner wall of the needle sleeve to release the clamping relation between the needle base and the needle sleeve, so it is realized that the core rod, the locking ring, and the needle base are all pulled into the needle sleeve.

Thus, for this safety syringe, the distal end of the core rod cooperates with the needle base via a transitional connection by means of the locking ring; after completion of injection, when it is intended to use the core rod to bring the needle base and the locking ring to move towards the needle sleeve on the proximal side, firstly, the core rod needs to bring the locking ring to move by a first distance to get the clamping hook of the locking ring to become hooked onto the hooking structure; after that, the core rod bring both the locking ring and the needle base to move together towards the proximal side of the needle sleeve. Hence, the retraction stroke of the core rod driving the needle base and the needle tube is long, the pulling force applied on the core rod is large, and meanwhile the syringe has a complicated structure.

SUMMARY OF THE INVENTION

Therefore, an actual technical problem to be solved by the present application is the defect of the safety syringe in prior art that the distal end of the core rod cooperates with the needle base via a transitional connection by means of the locking ring, the retraction stroke of the core rod driving the needle base and the needle tube is long, the pulling force applied on the core rod is large, and the syringe has a complicated structure.

For this, an aspect of the present application provides a safety syringe that comprises
- a needle sleeve, with a first groove provided on an inner wall thereof;
- a needle base, with at least two first claws provided on an outer wall thereof, the first claws being configured to clamp in the first groove;
- a core rod, sealedly and slidably arranged in the needle sleeve;
- wherein one of a proximal end of the needle base and a distal end of the core rod is provided with at least two second claws, and the other one is provided with a position-limiting member;
- the second claws are configured to abut against the position-limiting member along a slanted surface;
- in an injecting state, when the core rod slides towards a distal side, the second claws are forced to slide along the slanted surface and deform in a radial direction of the needle sleeve under the action of the slanted surface, so as to pass over the position-limiting member and become hooked onto the position-limiting member;
- in the injecting state or a retracting state, the core rod slides to drive the first claws to slip out of the first groove.

Optionally, in the afore-mentioned safety syringe, the second claws are arranged on the needle base or the core rod to protrude outwards; the position-limiting member is a position-limiting clamp ring; in the injecting state, the second claws contract in the radial direction of the needle sleeve under the action of the slanted surface to slide into an inner bore of the position-limiting clamp ring, so as to pass over the position-limiting clamp ring and become hooked onto the position-limiting clamp ring.

Optionally, in the afore-mentioned safety syringe, at least one first avoiding hole is provided in a side wall of the position-limiting clamp ring; in the injecting state, each of the second claws extends into a corresponding first avoiding hole in a one-to-one manner, so as to be hooked onto the side wall of the position-limiting clamp ring.

Optionally, in the afore-mentioned safety syringe, the second claws are provided on the proximal end of the needle base, the position-limiting clamp ring is provided on the distal end of the core rod; the needle base comprises a ring-shaped body, with an outer wall of the ring-shaped body being sealedly arranged on an inner wall of the needle sleeve, and an inner bore of the ring-shaped body being configured for mounting a needle tube;

at least two legs, evenly distributed on a same circle, with a distal end of each of the legs being fixed on a proximal end surface of the ring-shaped body;

wherein, the first claws and the second claws are fixed on and protrude from outer walls of the legs in a one-to-one manner, and each of the first claws is arranged between the ring-shaped body and a corresponding second claw;

in the injecting state, the second claws slide along the slanted surface to drive the legs to swing inwards in the radial direction of the needle sleeve, so as to bring the first claws out of the first groove.

Optionally, in the afore-mentioned safety syringe, at least three legs are provided, and all of the legs are evenly distributed on a same circle; and at least three first claws and at least three second claws are provided.

Optionally, in the afore-mentioned safety syringe, a groove wall at a proximal side of the first groove is in the form of a first position-limiting slope that is inclined from a groove mouth to a groove bottom; in the retracting state, the core rod slides towards a proximal side to drive the first claws to slip off the first position-limiting slope.

Optionally, in the afore-mentioned safety syringe, a mounting cavity of the needle sleeve comprises a needle base chamber and a transition chamber communicated with the needle base chamber; the transition chamber has an inner diameter larger than that of the needle base chamber, and a first stepped structure is formed between the needle base chamber and the transition chamber; and the needle base is arranged in the needle base chamber, with the legs passing through an inner bore of the first stepped structure, so that the second claws extend into the transition chamber.

Optionally, in the afore-mentioned safety syringe, a rubber plug is sleeved on an exterior of the core rod, and the core rod is slidably and sealedly arranged in the transition chamber by means of the rubber plug.

Optionally, in the afore-mentioned safety syringe, a proximal end of the rubber plug is fixed on the core rod, and under the action of a pressing force generated by the core rod sliding towards the distal side, a distal end of the rubber plug is closely pressed against a proximal end surface of the first stepped structure; at least one ring-shaped sealing protrusion is provided on an outer wall of the rubber plug, and the sealing protrusion along with the core rod is slidably and sealedly fitted on an inner wall of the transition chamber.

Optionally, in the afore-mentioned safety syringe, the first stepped structure comprises a first step and a second step in a ladder-shaped arrangement from the distal side to the proximal side; in the injecting state, a distal end surface of the position-limiting clamp ring abuts against a step surface of the first step, and a distal surface of the rubber plug abuts against a step surface of the second step.

Optionally, in the afore-mentioned safety syringe, the mounting cavity further comprises a position-limiting chamber communicated with a proximal end of the transition chamber; the position-limiting chamber has an inner diameter larger than that of the transition chamber, and a second stepped structure is formed between the transition chamber and the position-limiting chamber;

the safety syringe further comprises an elastic position-limiting ring fixed on an outer wall of the core rod; a position-limiting protrusion is provided on an inner wall of the position-limiting chamber; an outer diameter of the elastic position-limiting ring in a free state is at least larger than an inner diameter of a proximal end of the transition chamber, and is also larger than an inner diameter of the position-limiting protrusion;

in the retracting state, a proximal end of the elastic position-limiting ring is constrained in the position-limiting chamber by a proximal end face of the second stepped structure, and a distal end of the elastic position-limiting ring abuts against the position-limiting protrusion.

Optionally, in the afore-mentioned safety syringe, a gap is provided in a circumferential wall of the elastic position-limiting ring.

Optionally, the afore-mentioned safety syringe further comprises a clamp sleeved on an exterior of the core rod and arranged in the position-limiting chamber; an annular boss is provided on an outer wall of the clamp, and an outer circumferential wall of the annular boss is fitted on an inner wall of the position-limiting chamber; in the retracting state, the elastic position-limiting ring is driven by the sliding of the core rod such that the proximal end of the elastic position-limiting ring abuts against the annular boss to push the clamp to move towards the position-limiting protrusion until the clamp abuts against the position-limiting protrusion.

Optionally, in the afore-mentioned safety syringe, the second stepped structure comprises a third step and a fourth step in a ladder-shaped arrangement from the distal side to the proximal side; in the injecting state, a distal end surface of the clamp abuts against a step surface of the third step, and the annular boss abuts against a step surface of the fourth step; in the retracting state, the distal end of the elastic position-limiting ring is able to abut against the step surface of the third step.

Optionally, in the afore-mentioned safety syringe, the transition chamber comprises a straight cylindrical segment and a first throat segment fixed on a proximal end of the straight cylindrical segment, the first throat segment has an inner diameter that gradually decreases in a direction from the distal side to the proximal side; the outer diameter of the elastic position-limiting ring in the free state is larger than the inner diameter of the first throat segment, and is smaller than or equal to an inner diameter of the straight cylindrical segment.

Optionally, in the afore-mentioned safety syringe, an annular groove is provided on an outer wall of the core rod, and a breakable site is formed at a groove bottom of the annular groove.

The technical solution of the present application has the following advantages:

1. The safety syringe provided by the present application comprises a needle sleeve, a needle base, a needle tube and a core rod. First claws on an outer wall of the needle base are configured to clamp in a first groove on an inner wall of the needle sleeve, thereby mounting the needle base onto the inner wall of the needle sleeve; one of a proximal end of the needle base and a distal end of the core rod is provided with at least two second claws, and the other one thereof is provided with a position-limiting member; the second claws are configured to abut against the position-limiting member along a slanted surface.

When the core rod slides towards a distal side to perform injection, the second claws are forced to slide along the slanted surface, the slanted surface exerts an acting force on the second claws, with a first force component in a radial direction of the needle sleeve and a second force component in an axial direction of the needle sleeve, wherein, under the action of the first force component, the second claws contract or expand in the radial direction of the needle sleeve, and under the action of the second force component, the second claws slide to pass over the position-limiting member; then, the acting force exerted by the slanted surface on the second claws is released, so that the second claws restore their position in the radial direction and become hooked onto the position-limiting member, thereby realizing interlocking of the needle base and the core rod, and during this process, the core rod slides to indirectly exert an acting force on the first claws so as to drive the first claws to slip out of the first groove; or when performing retraction of the core rod after completion of the injection, because the second claws are locked on the position-limiting member, as the core rod slides towards a proximal side, the core rod exerts a pulling force on the needle base towards the proximal side, so as to force the first claws to slip out of the first groove, thereby separating the needle base from the needle sleeve; after that, the needle base slides towards the proximal side together with the core rod, thereby shortening the retraction stroke of the core rod, only a small retraction pulling force is required, and there is no need to arrange a locking ring, which simplifies the structure of the overall safety syringe, and also makes it easy to manufacture the safety syringe.

2. In the safety syringe provided by the present application, the second claws are arranged on the needle base or the core rod to protrude outwards; the position-limiting member is a position-limiting clamp ring; in the injecting state, the second claws contract in the radial direction of the needle sleeve under the action of the slanted surface to slide into an inner bore of the position-limiting clamp ring, so as to become hooked onto the position-limiting clamp ring in a radially outward direction, thereby realizing interlocking of the needle base and the core rod.

3. In the safety syringe provided by the present application, at least one first avoiding hole is provided in a side wall of the position-limiting clamp ring; in the injecting state, each of the second claws extends into a corresponding first avoiding hole in a one-to-one manner, so as to be hooked onto the side wall of the position-limiting clamp ring, thereby ensuring the firmness of the interlocking between the second claws and the position-limiting clamp ring.

4. In the safety syringe provided by the present application, the second claws are provided on the proximal end of the needle base, the position-limiting clamp ring is provided on the distal end of the core rod; the needle base comprises a ring-shaped body and at least two legs, wherein, the first claws and the second claws are fixed on and protrude from outer walls of the legs in a one-to-one manner, and each of the first claws is arranged between the ring-shaped body and a corresponding second claw; in the injecting state, when the second claws slide along the slanted surface towards the inner bore of the position-limiting clamp ring, the legs are driven to swing inwards in the radial direction of the needle sleeve, so that the first claws moves together with the legs in the radially inward direction, which brings the first claws out of the first groove, therefore, in the retraction process for the safety syringe, only a very small pulling force is required to pull both the needle base and the needle tube together with the core rod towards the proximal side of the needle sleeve.

5. In the safety syringe provided by the present application, the mounting cavity further comprises a position-limiting chamber communicated with a proximal end of the transition chamber; the position-limiting chamber has an inner diameter larger than that of the transition chamber, and a second stepped structure is formed between the transition chamber and the position-limiting chamber; the safety syringe further comprises an elastic position-limiting ring fixed on an outer wall of the core rod; a position-limiting protrusion is provided on an inner wall of the position-limiting chamber; an outer diameter of the elastic position-limiting ring in a free state is at least larger than an inner diameter of a proximal end of the transition chamber, and is also larger than an inner diameter of the position-limiting protrusion.

In the retracting state, the core rod drives the elastic position-limiting ring to move synchronously, the elastic position-limiting ring is radially pressed at the proximal end of the transition chamber to contract, and then radially restores its position after entering the position-limiting chamber, wherein a proximal end of the elastic position-limiting ring is constrained in the position-limiting chamber by a distal end face of the second stepped structure, and a distal end of the elastic position-limiting ring abuts against the position-limiting protrusion, so that the core rod becomes unable to slide relative to the needle sleeve, and the position of the core rod is locked relative to the needle sleeve, thereby completely prevent second-time reuse of the safety syringe.

BRIEF DESCRIPTION OF THE DRAWINGS

In order to describe the technical solutions in the specific embodiments of the present application or in the prior art more clearly, hereinafter, the appended drawings used for describing the specific embodiments or the prior art will be briefly introduced. Apparently, the appended drawings described below are only some embodiments of the present invention, and for a person with ordinary skill in the art, without expenditure of creative labor, other drawings can be derived based on these appended drawings.

FIG. 6b is a stereoscopic view of the longitudinal section at the proximal end of the needle sleeve in FIG. 6a;

FIG. 6c is a schematic diagram of the longitudinal section at the proximal end of the needle sleeve in FIG. 6a;

FIG. 6d is a schematic diagram of the longitudinal section at the distal end of the needle sleeve in FIG. 6a;

REFERENCE SIGNS

1—needle sleeve, 11—needle base chamber, 111—first groove, 111a—third slanted surface, 12—transition chamber, 13—position-limiting chamber, 131—position-limiting protrusion;
2—core rod, 21—position-limiting clamp ring, 211—second slanted surface, 212—first avoiding hole, 22—third annular groove, 23—breakable site, 24—annular snap-fit groove;
3—needle base, 31—ring-shaped body, 311—second annular groove, 312—sealing ring, 32—leg, 33—second claw, 331—first slanted surface, 34—first claw;
4—needle tube;
5—rubber plug, 51—sealing protrusion, 52—fitting protrusion;
6—elastic position-limiting ring;
7—clamp, 71—annular boss, 72—first conical surface, 73—second conical surface;
8—protection sheath;
9—first stepped structure, 91—first step, 101a—third conical surface, 92—second step, 102b—fourth conical surface;
10—second stepped structure, 101—third step, 102—fourth step.

DETAILED DESCRIPTION OF EMBODIMENTS

A clear and complete description of the technical solution of the present application is given below, in conjunction with the appended drawings. Apparently, the described embodiments are part of, but not all of, the embodiments of the present application. All the other embodiments, obtained by a person with ordinary skill in the art based on the embodiments in the present application without expenditure of creative labor, belong to the protection scope of the present application.

In the description of the present application, it should be noted that, unless specifically defined or restricted otherwise, terms such as "mount", "interconnect", "connect" should be broadly construed, for example, it may be a fixed connection, a detachable connection, or an integral connection; it may be either a direct connection or an indirect connection through an intermediate medium, or it may be an internal communication between two units. For a person skilled in the art, the specific meaning of the above terms in the present application may be understood according to specific situations thereof.

In addition, the technical features involved in different embodiments of the present application described below may be combined with one another as long as they do not conflict with one another.

Embodiment 1

Figure 1:
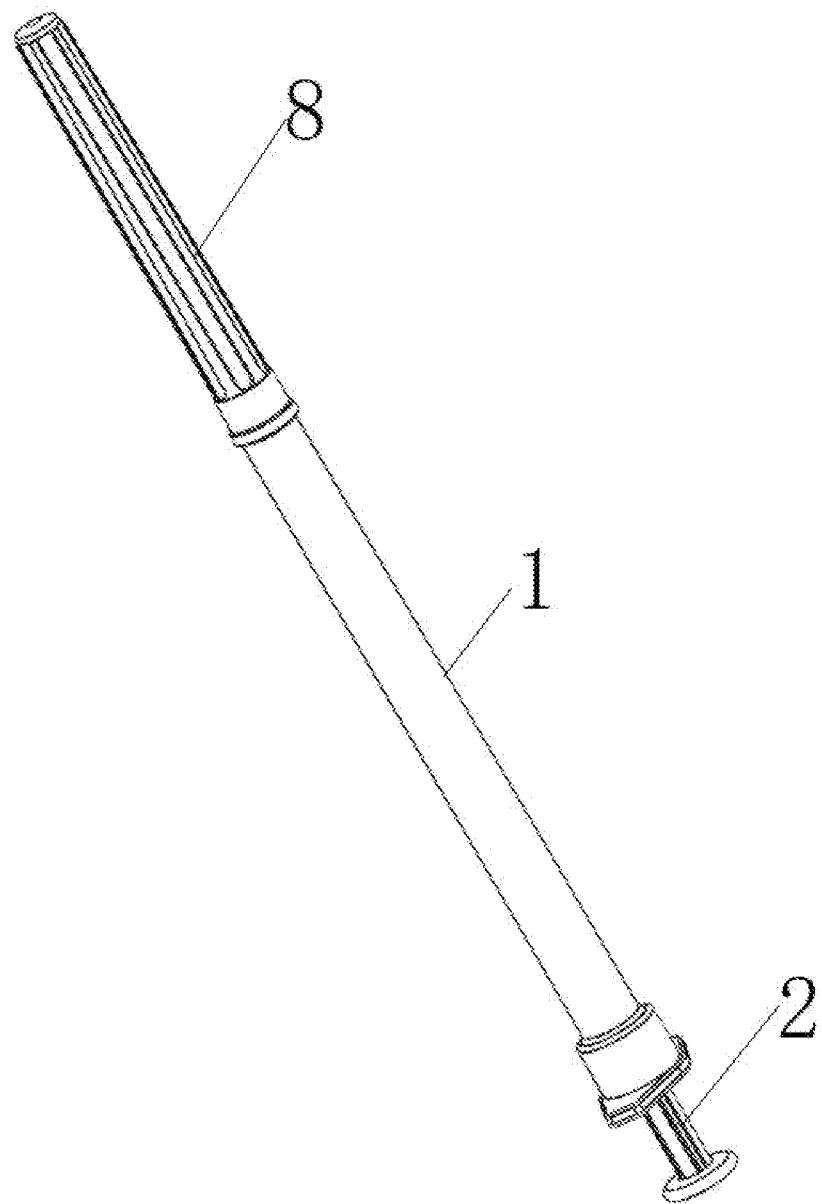
FIG. 1 is a stereoscopic structural schematic diagram of a safety syringe provided in Embodiment 1 of the present application.
Figure 2:
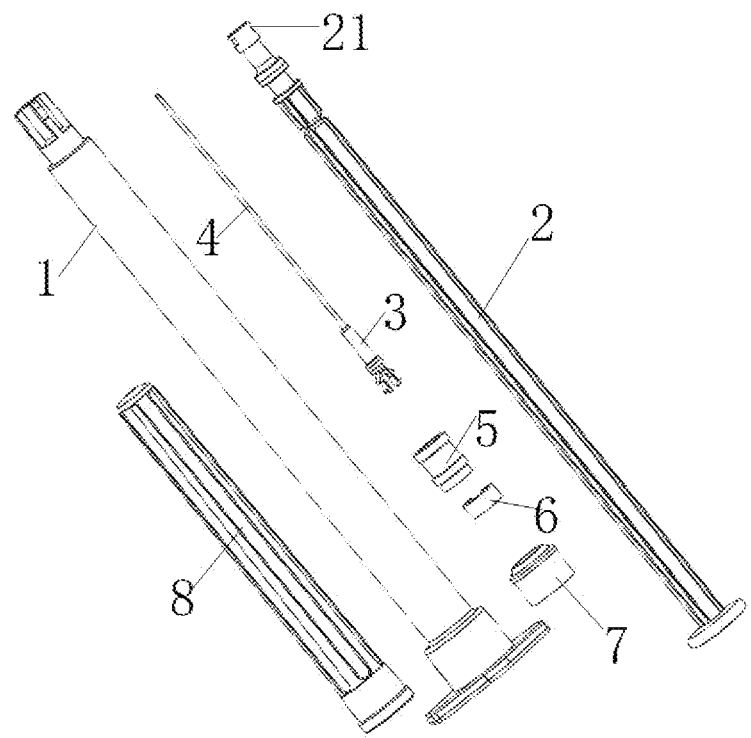
FIG. 2 is an exploded view of the safety syringe in FIG. 1.

The present embodiment provides a safety syringe, as shown in FIG. 1 and FIG. 2, the safety syringe comprises a needle sleeve 1, a needle base 3, a needle tube 4 and a core rod 2.

Figure 3:
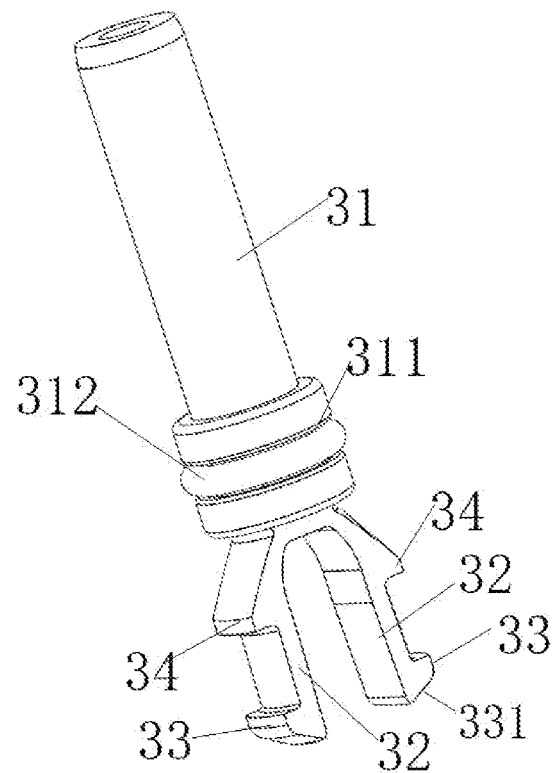
FIG. 3 is a structural schematic diagram of the needle base in FIG. 1.
Figure 6A:
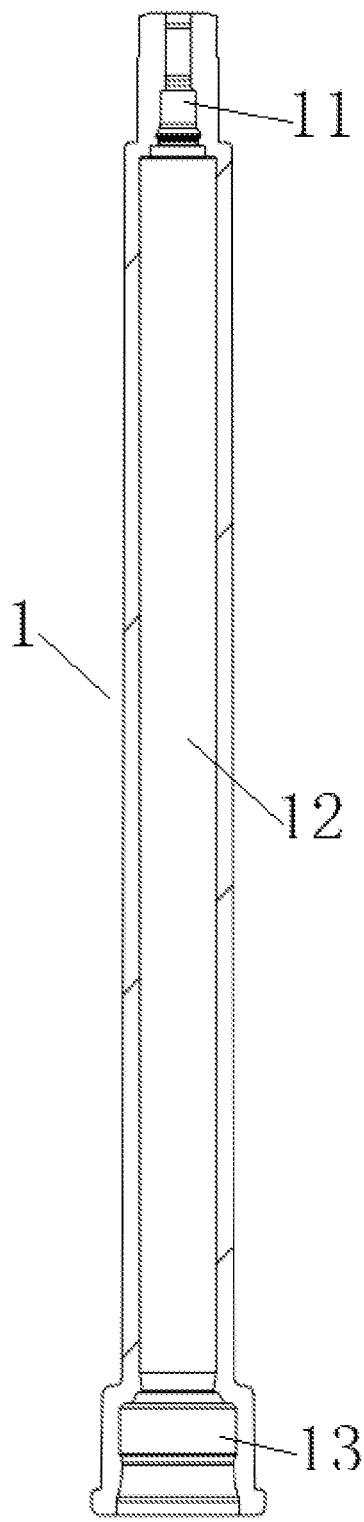
FIG. 6a is a longitudinal sectional view of the needle sleeve in FIG. 1.
Figure 6B:
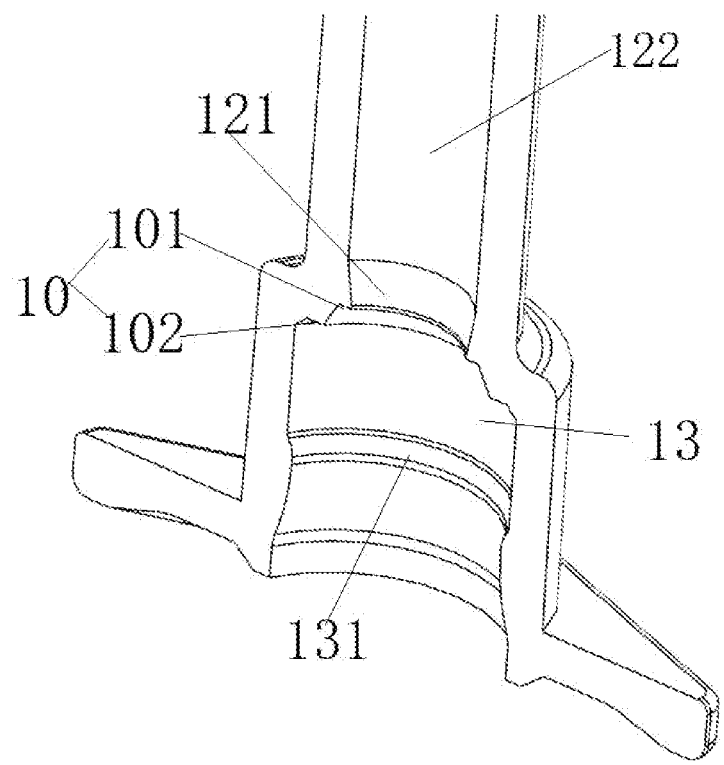
Figure 6C:
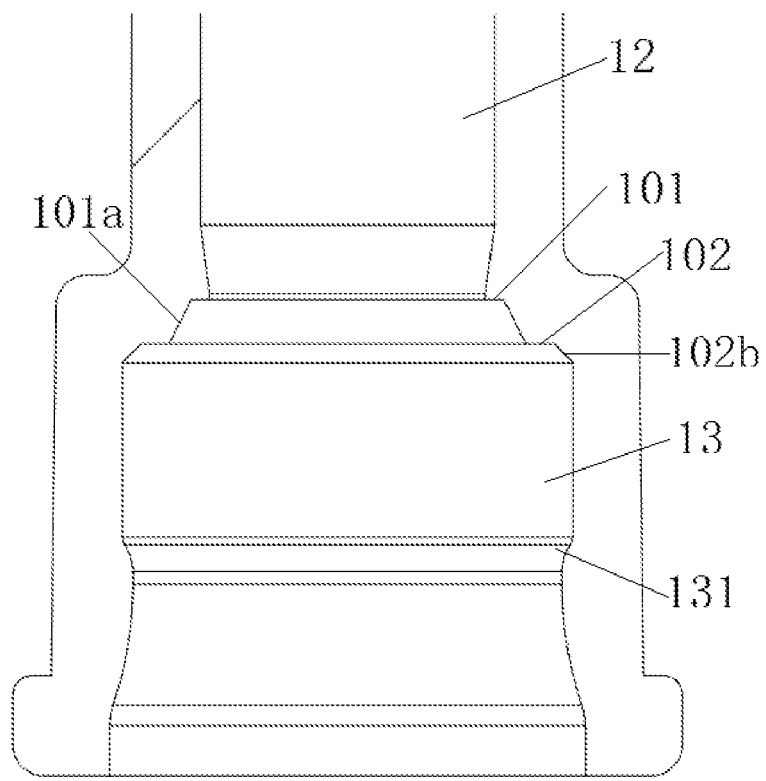
Figure 6D:
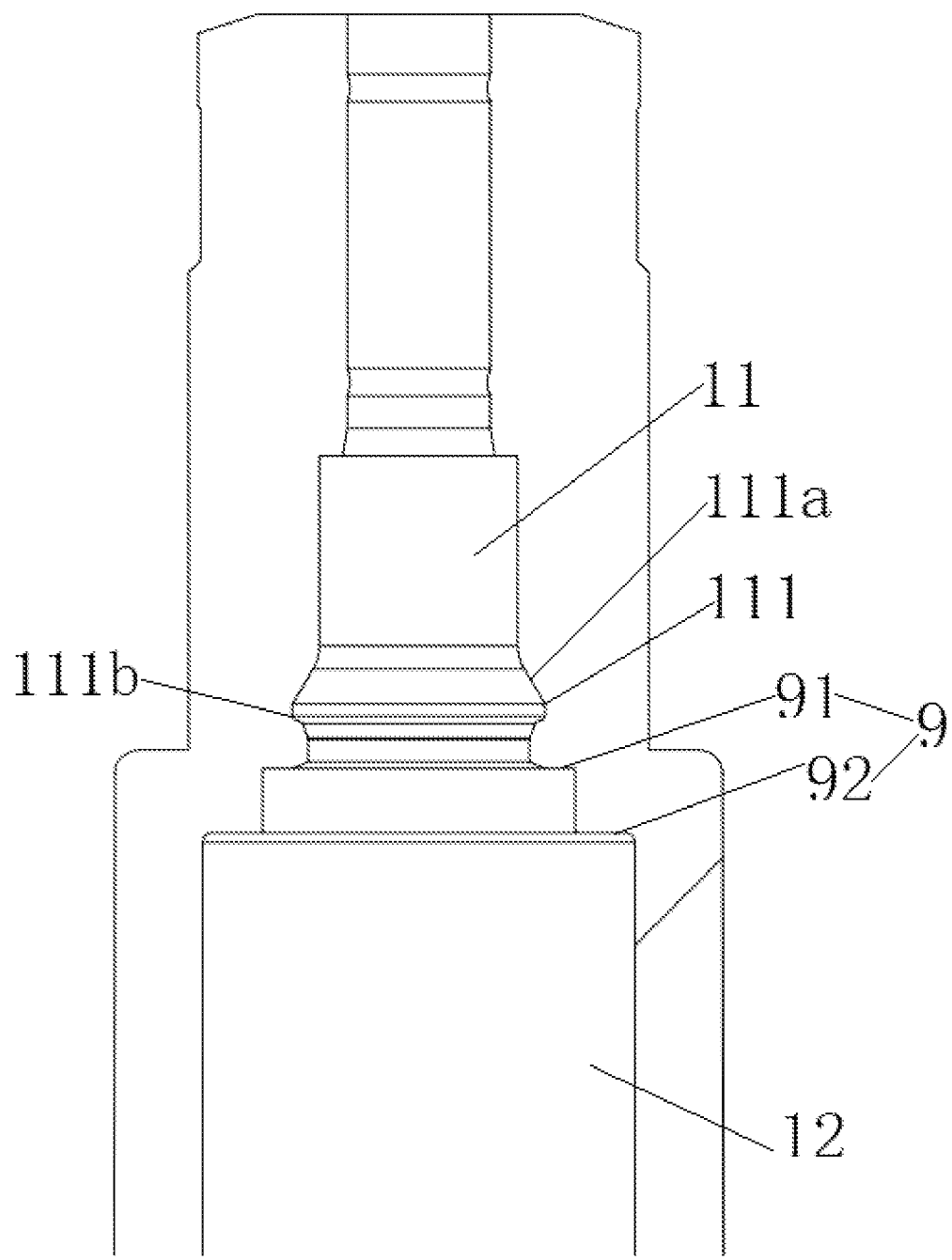

Wherein, the needle sleeve 1 has a mounting cavity; as shown in FIG. 6d, a first groove 111 is provided on an inner wall of the mounting cavity; a distal end of the needle base 3 is configured for mounting the needle tube 4; as shown in FIG. 3, at least two first claws 34 are provided on an outer wall of the needle base 3, and the first claws 34 are configured to clamp in the first groove 111; the core rod 2 is sealedly and slidably arranged in the needle sleeve 1; one of a proximal end of the needle base 3 and a distal end of the core rod 2 is provided with at least two second claws 33, and the other one thereof is provided with a position-limiting member; the second claws 33 are configured to abut against the position-limiting member along a slanted surface.

The proximal side and distal side in this embodiment are with reference to a person operating the syringe, wherein a side close to the operation end of the core rod is the proximal side, and a side of the core rod close to the needle tube is the distal side.

When the core rod 2 slides towards the distal side to perform injection, the second claws 33 are forced to slide along the slanted surface, the slanted surface exerts an acting force on the second claws 33, with a first force component in a radial direction of the needle sleeve 1 and a second force component in an axial direction of the needle sleeve 1, wherein, under the action of the first force component, the second claws 33 contract or expand in the radial direction of the needle sleeve 1, and under the action of the second force component, the second claws 33 slide in the axial direction of the needle sleeve to pass over the position-limiting member; then, the acting force exerted by the slanted surface on the second claws 33 is released, so that the second claws 33 restore their position in the radial direction and become hooked onto the position-limiting member, thereby realizing interlocking of the needle base 3 and the core rod 2, and during this process, the core rod slides to indirectly exert an acting force on the first claws so as to drive the first claws to slip out of the first groove (the first way for the first claws to slip off the first groove); or when performing retraction of the core rod 2 after completion of the injection, because the second claws 33 are locked on the position-limiting member, as the core rod 2 slides towards the proximal side, the core rod 2 exerts a pulling force on the needle base 3 towards the proximal side so as to force the first claws 34 to slip out of the first groove 111 (the second way for the first claws to slip off the first groove), thereby separating the needle base 3 from the needle sleeve 1; after that, the needle base 3 slides towards the proximal side together with the core rod 2, thereby shortening the retraction stroke of the core rod 2, only a small retraction pulling force is required, and there is no need to arrange a locking ring, which simplifies the structure of the overall safety syringe.

Figure 4:
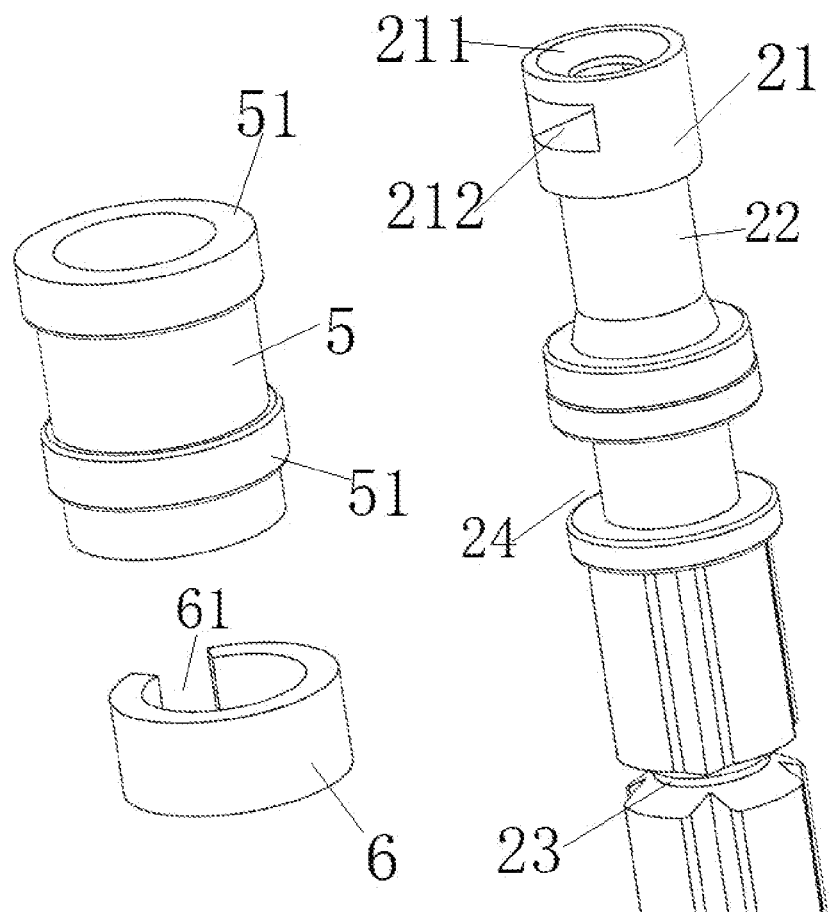
FIG. 4 is an exploded view of the rubber plug, the position-limiting ring, and part of the core rod in FIG. 1.

As shown in FIG. 3, the second claws 33 are arranged on the needle base 3 to protrude outwards; as shown in FIG. 4, the position-limiting member is a position-limiting clamp ring 21 fixed on the core rod 2, an end face at a proximal end of each second claw 33 is a first slanted surface 331, a distal end of the position-limiting clamp ring 21 has a second slanted surface 211, the first slanted surface 331 and the second slanted surface 211 are configured to abut against each other in parallel; an inclination angle of the first slanted surface 331 is consistent with an inclination angle of the second slanted surface 211, and in the radial direction of the needle sleeve 1 in FIG. 4 and FIG. 3, the first slanted surface 331 and the second slanted surface 211 both incline downwards from an outer side to an inner side.

In an injection process, the core rod 2 drives the position-limiting clamp ring 21 to slide towards the distal side, the second slanted surface 211 of the position-limiting clamp ring 21 slides along the first slanted surface 331 of each second claws 33, so that the second claws 33 contract in the radial direction of the needle sleeve under the action of the second slanted surface 211 to slide into an inner bore of the position-limiting clamp ring 21; when the first slanted surface 331 of each second claws 33 becomes separated from the second slanted surface 211 of the core rod 2, the second claws 33 are no longer under the action of the second slanted surface 211 of the position-limiting clamp ring 21 and thus restore their position in the radial direction, so that the second claws 33 become hooked onto a proximal end face of the position-limiting clamp ring 21, thereby realizing the interlocking cooperation of the needle base 3 and the core rod 2.

As alternatives, for the afore-mentioned slanted surface, there may only be a second slanted surface 211 provided on the position-limiting clamp ring 21, or there may only be first slanted surfaces 331 provided on the second claws 33, in these cases, during the sliding process of the core rod 2, the second claws 33 can also realize radial contraction deformation under the action of the slanted surface, so as to cause the second claws 33 to become hooked onto the position-limiting clamp ring 21.

In the implementing ways described below, the structure of the safety syringe is described in detail by illustrating an example wherein the position-limiting clamp ring 21 is fixed on the core rod 2, and the second claws 33 are fixed on the needle base 3.

As for the structure of the position-limiting clamp ring 21, as shown in FIG. 4, preferably, at least one first avoiding hole 212 is provided in a side wall of the position-limiting clamp ring 21; for example, there are two second claws 33, and correspondingly there are two first avoiding holes 212; in the injecting state, each of the second claws 33 extends into a corresponding first avoiding hole 212, so as to be hooked onto the side wall of the position-limiting clamp ring 21, thereby ensuring the firmness of the interlocking between the second claws 33 and the position-limiting clamp ring 21 on the core rod 2.

As alternatives, when there are a plurality of second claws 33, for example, there are three, four, five, six or more second claws 33, the plurality of second claws 33 are distributed on a same circle, and correspondingly, there are a plurality of first avoiding holes 212, each of the second claws 33 extends into a corresponding first avoiding hole 212 in a one-to-one manner, so as to be hooked onto the side wall of the position-limiting clamp ring.

As for the structure of the needle base 3, preferably, as shown in FIG. 3, the needle base 3 comprises a ring-shaped body 31 and at least two legs 32, an outer wall of the ring-shaped body 31 is sealedly arranged in the mounting cavity; the ring-shaped body 31 has an inner bore configured for mounting the needle tube 4; wherein the at least two legs 32 are evenly distributed on a same circle, with a distal end of each of the legs 32 being fixed on a proximal end surface of the ring-shaped body 31; the first claws 34 and the second claws 33 are fixed on and protrude from outer walls of the legs 32 in a one-to-one manner, and each of the first claws 34 is arranged between the ring-shaped body 31 and a corresponding second claw 33, so that the first claws 34 and the second claws 33 form two stages of claws on each of the legs 32. Most preferably, the ring-shaped body, the legs, the first claws, and the second claws of the afore-mentioned needle base are integrally formed in one piece, all of which are made of medical plastics, therefore, at the same time of simplifying the structure of the safety syringe, it makes it easy to manufacture the safety syringe, for example, by injection molding. Of course, other medical materials may also be used.

Preferably, there are a plurality of legs 32 on the needle base 3, and preferably, the plurality of legs 32 are evenly distributed on a same circle and fixed on the proximal end surface of the ring-shaped body 31; correspondingly, there are a plurality of first claws 34 and a plurality of second claws 33, each first claw 34 and each second claw 33 are fixed on an outer wall of each leg 32 in a one-to-one manner. By the arrangement of multiple legs 32 and multiple second claws 33, when the second claws 33 are hooked onto the position-limiting clamp ring 21 for locking, multiple locking sites are formed, thereby further ensuring the firmness of the interlocking between the needle base 3 and the core rod 2.

Because the two legs are spaced apart by a distance, when the second claws 33 are under the action of the second slanted surface 211 on the position-limiting clamp ring 21 during sliding, it can drive the two legs 32 to swing inwards in the radial direction of the needle sleeve relative to the ring-shaped body 31 around the distal end of each leg, the legs 32 bring the first claws 34 to move inwards in the radial direction, so as to force the first claws 34 out of the first groove 111, so it is realized that, in the injecting state, the sliding of the core rod can bring the first claws to slip out of the first groove; therefore, in the retraction process of the core rod 2, only a very small pulling force, which causes the second claws 33 to slide along the second slanted surface 211, is required to realize separation of the first claws 34 from the first groove 111, thereby facilitating the retraction of the needle base 3 together with the core rod 2. Herein, a radial force is applied to cause the legs 32 to swing inwards in the radial direction to force the first claws 34 to become separated from the first groove 111.

Preferably, a groove wall at a proximal side of the first groove 111 is in the form of a guiding curved surface that is inclined from a groove mouth to a groove bottom, i.e., a first position-limiting slope 111b, for example, in FIG. 6d, the guiding curved surface inclines towards the axis of the needle sleeve 1 from an upper side to a lower side, thereby further helping the first claws slip out of the first groove along the first position-limiting slope when the legs swing inwards.

As an alternative, the afore-mentioned needle base may be provided with no legs, and the first claws and the second claws are directly arranged on the ring-shaped body 31; in the injection process, the second slanted surface of the core rod exerts an acting force on the second claws, but cannot force the first claws out of the first groove; herein, a groove wall at a proximal side of the first groove is the afore-mentioned first position-limiting slope 111b, and during the retraction process, when a pulling force towards the proximal side is exerted on the core rod 2, because the needle base is interlocked with the core rod, under this pulling force, the first claws 34 on the needle base 3 would slip out of the first groove 111 along the guiding curved surface, that is, an axial acting force can separate the first claws 34 from the first groove 111, thereby realizing the retraction action.

As for the first groove 111, as shown in FIG. 6a, a groove wall at a distal side of the first groove 111 is in the form of a third slanted surface 111a inclined from a groove mouth to a groove bottom; correspondingly, an outer wall of each first claw 34 is provided with a fourth slanted surface configured to abut closely against the third slanted surface 111a. That is, an outer peripheral surface at the distal side of each first claw 34 is in the form of a conical surface, the conical surface of each first claw 34 abuts closely against the third slanted surface 111a of the first groove 111, which enhances the hermetic tightness at the connection between the first claws 34 and the first groove 111.

Preferably, the afore-mentioned first groove 111 has an inner wall shape that matches an outer wall shape of each first claw 34, so that, when each first claw 34 clamps into the first groove 111, the two can completely fit against each other, so as to enhance the hermetic tightness at the connection.

As for the mounting cavity of the needle sleeve 1, as shown in FIG. 6a, the mounting cavity comprises a needle base chamber 11 and a transition chamber 12 sequentially arranged from the distal side to the proximal side and communicated with each other; the transition chamber 12 has an inner diameter larger than that of the needle base chamber 11, and a first stepped structure 9 is formed between the needle base chamber 11 and the transition chamber 12; wherein the needle base 3 is mounted in the needle base chamber 11, and the afore-mentioned first groove 111 is provided on an inner wall of the needle base chamber 11.

Preferably, an annular step is provided on the inner wall of the needle base chamber 11, and correspondingly, as shown in FIG. 3, an outer circumferential wall of the afore-mentioned ring-shaped body 31 is provided with a flange protruding radially outwards, a second annular groove 311 is arranged on the flange, and the flange is configured to abut against a step surface of the annular step, a sealing ring 312 is fitted in the second annular groove 311 to realize a sealed connection between the needle base 3 and the needle base chamber 11; meanwhile, the annular step limit the position of the needle base 3 inside the needle base chamber 11. A proximal end of the needle tube 4 is inserted in the inner bore of the ring-shaped body 31, and a distal end of the needle tube 4 extends out from a distal end of the needle sleeve 1.

As shown in FIG. 1 and FIG. 2, a protection sheath 8 is sleeved on an outer wall of the needle sleeve 1 at the part where the needle base chamber 11 is located, so as to have a protection effect for the needle tube 4. The protection sheath 8 can be fixed to the needle sleeve 1 in a variety of ways, such as threaded fit or snap fit, or other existing fitting manner.

Figure 7A:
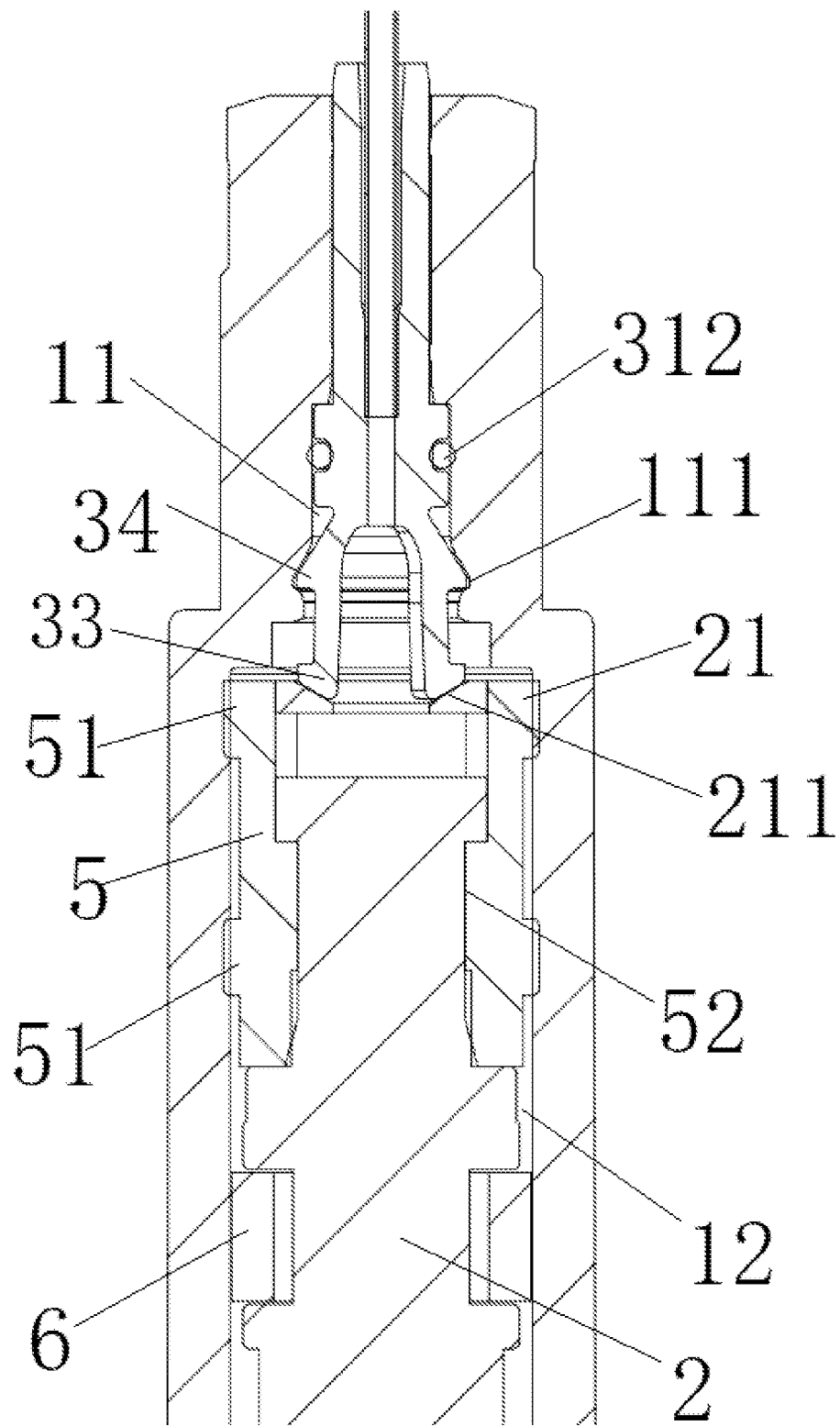
FIG. 7a is a schematic diagram of a status of the needle base and the distal end of the core rod when the safety syringe in FIG. 1 is not yet used for injection.

As for the core rod 2, as shown in FIG. 7a, a rubber plug 5 is sleeved on an exterior of the core rod 2, and the core rod 2 is slidably and sealedly arranged in the transition chamber 12 by means of the rubber plug 5, with the legs passing through an inner bore of the first stepped structure 9, so that the second claws 33 extend into the transition chamber 12.

As shown in FIG. 7a, preferably, a proximal end of the rubber plug 5 is fixed on the core rod 2, and under the action of a pressing force generated by the core rod 2 sliding towards the distal side, a distal end of the rubber plug 5 is closely pressed against a proximal end surface of the first stepped structure 9; at least one ring-shaped sealing protrusion 51 is provided on an outer wall of the rubber plug 5, and the sealing protrusion 51 along with the core rod 2 is slidably and sealedly fitted on an inner wall of the transition chamber 12.

Preferably, as shown in FIG. 4, a third annular groove 22 is provided on an outer wall of the core rod 2, and an inner wall of the rubber plug 5 is provided with an annular fitting protrusion 52 protruding radially inwards, as shown in FIG. 7a, the fitting protrusion 52 is lodged in the third annular groove 22, and two sealing protrusions 51 are provided on the outer wall of the rubber plug 5, one of the sealing protrusions 51 is located at a distal end of the rubber plug 5 on the outer wall thereof; the distal end of the rubber plug 5 is sleeved on an outer wall of the position-limiting clamp ring 21 but does not extend farther than the distal end face of the position-limiting clamp ring 21.

Figure 8:
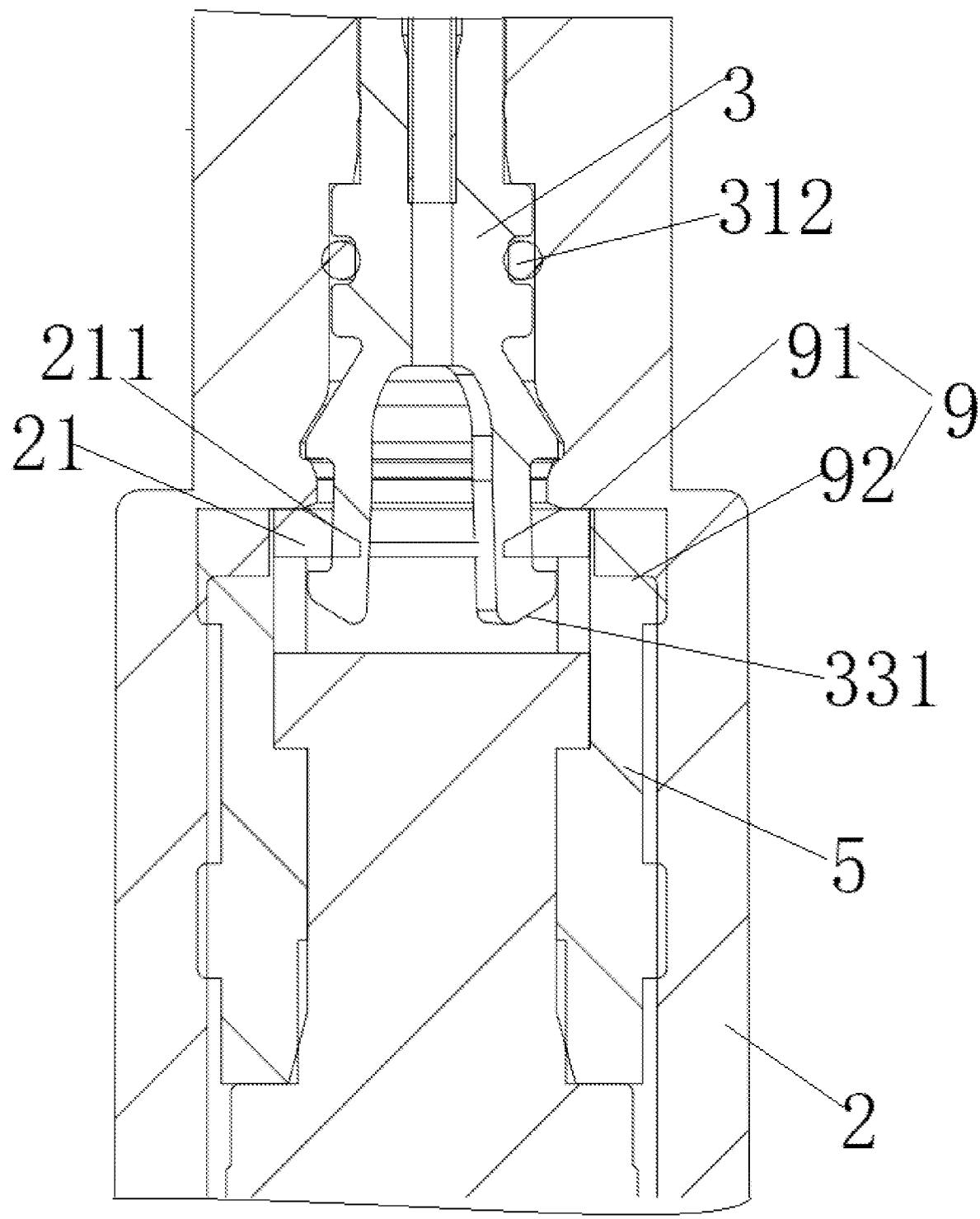
FIG. 8 is a schematic diagram of a status of the needle base and the distal end of the core rod when the safety syringe in FIG. 1 has completed injection.

As shown in FIG. 6d, the first stepped structure 9 comprises a first step 91 and a second step 92 in a ladder-shaped arrangement from the distal side to the proximal side, and as shown in FIG. 8, in the injecting state, a distal end surface of the position-limiting clamp ring 21 abuts against a step surface of the first step 91, so that the rubber plug 5 is pressed to deform in the axial direction of the needle sleeve 1, and a distal surface of the rubber plug 5 abuts against a step surface of the second step 92, the sealing protrusions 51 are sealed on the inner wall of the transition chamber 12, so it is realized that, in the injecting state, a sealed connection is established between the core rod 2 and the inner wall of the transition chamber 12.

Further preferably, as shown in FIG. 8, the position-limiting clamp ring 21 has an outer diameter equal to a diameter of an inner bore of the first step 91, the outer wall of the position-limiting clamp ring 21 fits on a wall of the inner bore of the first step 91, and the position-limiting clamp ring 21 has an axial height consistent with that of the inner bore of the first step 91, thereby further making the two closely fit against each other.

As shown in FIG. 6a, the mounting cavity further comprises a position-limiting chamber 13 communicated with a proximal end of the transition chamber 12; the position-limiting chamber 13 has an inner diameter larger than that of the transition chamber 12, and a second stepped structure 10 is formed between the transition chamber 12 and the position-limiting chamber 13.

As shown in FIG. 4, the safety syringe further comprises an elastic position-limiting ring 6 fixed on an outer wall of the core rod 2. For example, the outer wall of the core rod 2 is provided with a first annular flange and a second annular flange, with an annular snap-fit groove 24 formed between the two annular flanges; the elastic position-limiting ring 6 is sleeved in the annular snap-fit groove 24, with the two ends of the elastic position-limiting ring respectively abut against the first annular flange and a second annular flange. As shown in FIG. 6b and FIG. 6c, a position-limiting protrusion 131 is provided on an inner wall of the position-limiting chamber 13.

As for the elastic position-limiting ring 6, as shown in FIG. 4, a gap 61 is provided in a circumferential wall of the elastic position-limiting ring 6, so that the elastic position-limiting ring 6 has a radially deformable space; an outer diameter of the elastic position-limiting ring 6 in a free state is at least larger than an inner diameter of a proximal end of the transition chamber 12, and is also larger than an inner diameter of the position-limiting protrusion 131.

During the injection process, the elastic position-limiting ring 6 moves together with the core rod 2 towards the distal side, and when the elastic position-limiting ring 6 is pressed by an inner wall of the proximal end of the transition chamber 12, the two ends of the gap of the elastic position-limiting ring 6 moves closer to each other in the circumferential direction, so the elastic position-limiting ring 6 contracts radially, with an increased deformable space as compared to the detents in prior art, and after that, an outer wall of the elastic position-limiting ring 6 abuts against the inner wall of the transition chamber 12 so as to reduce friction between the elastic position-limiting ring 6 and the inner wall of the transition chamber 12, therefore, in the retraction process, a small pulling force is needed to allow the core rod 2 bring the elastic position-limiting ring 6 to slide towards the proximal side; after the elastic position-limiting ring 6 slides into the position-limiting chamber 13, because it is no longer under the action of radial pressing force, the two ends of the gap 61 of the elastic position-limiting ring 6 move away from each other in the circumferential direction, so the elastic position-limiting ring 6 restores its initial state, thus, a distal end of the elastic position-limiting ring 6 is constrained in the position-limiting chamber 13 by a proximal end face of the transition chamber 12 (i.e., a proximal end face of the second stepped structure 10), and a proximal end of the elastic position-limiting ring 6 abuts against the position-limiting protrusion 131, and when the core rod 2 moves again towards the distal side, an end face of the elastic position-limiting ring 6 forms a surface contact with the proximal end face of the transition chamber 12, so the elastic position-limiting ring 6 is not easily damaged, and the core rod 2 can hardly move again towards the distal side, therefore, it is ensured that the core rod 2 cannot once again be injected and retracted relative to the needle sleeve 1, which makes the safety level of the safety syringe high.

Preferably, for example, as shown in FIG. 6b, the transition chamber 12 comprises a straight cylindrical segment 122 and a first throat segment 121 fixed on a proximal end of the straight cylindrical segment 122, the first throat segment has an inner diameter that gradually decreases in a direction from the distal side to the proximal side; the outer diameter of the elastic position-limiting ring 6 in its free state is larger than the inner diameter of the first throat segment, and is smaller than or equal to an inner diameter of the straight cylindrical segment 122. That is, the inner wall of the first throat segment 121 forms a second position-limiting slope.

When the core rod 2 is being retracted, firstly, the elastic position-limiting ring 6 moves together with the core rod 2 in the straight cylindrical segment 122 of the transition chamber 12, with no radial contraction of the elastic position-limiting ring 6; when the elastic position-limiting ring 6 slides to an inner bore of the first throat segment 121, the elastic position-limiting ring 6 is pressed by a wall of the inner bore of the first throat segment to contract radially, until the core rod 2 brings the elastic position-limiting ring 6 into the position-limiting chamber 13, then, the elastic position-limiting ring 6 radially restores its position, wherein the distal end of the elastic position-limiting ring 6 is constrained in the position-limiting chamber by the proximal end of the second stepped structure 10, and a proximal end of the elastic position-limiting ring 6 abuts against the position-limiting protrusion 131, herein, because the distal end of the second stepped structure 10 has an inner diameter equal to that of the proximal end of the first throat segment, the core rod 2 is constrained onto the needle sleeve 1, and the core rod 2 becomes unable to slide towards the proximal side or towards the distal side, thereby completely prevent second-time reuse of the safety syringe. During the entire retraction process, the elastic position-limiting ring 6 is only pressed to contract radially at the first throat segment, so that the friction between the outer wall of the elastic position-limiting ring 6 and the transition chamber 12 is further reduced, thereby reducing the retraction pulling force.

Figure 5:
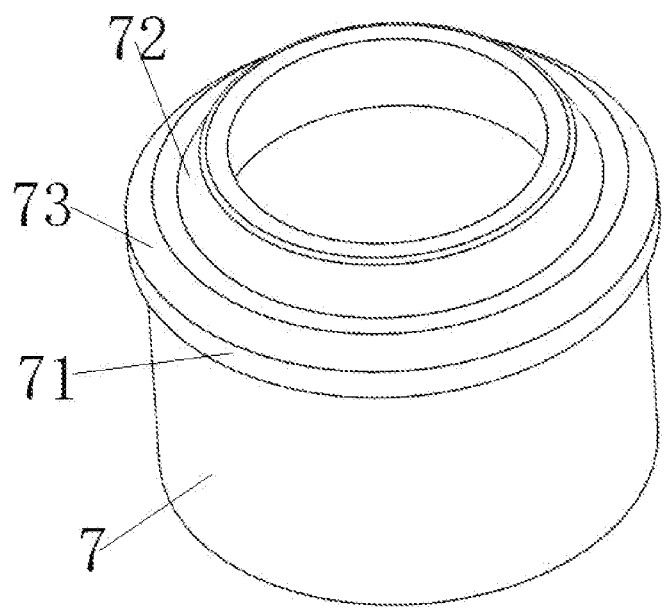
FIG. 5 is a structural schematic diagram of the clamp in FIG. 1.
Figure 7B:
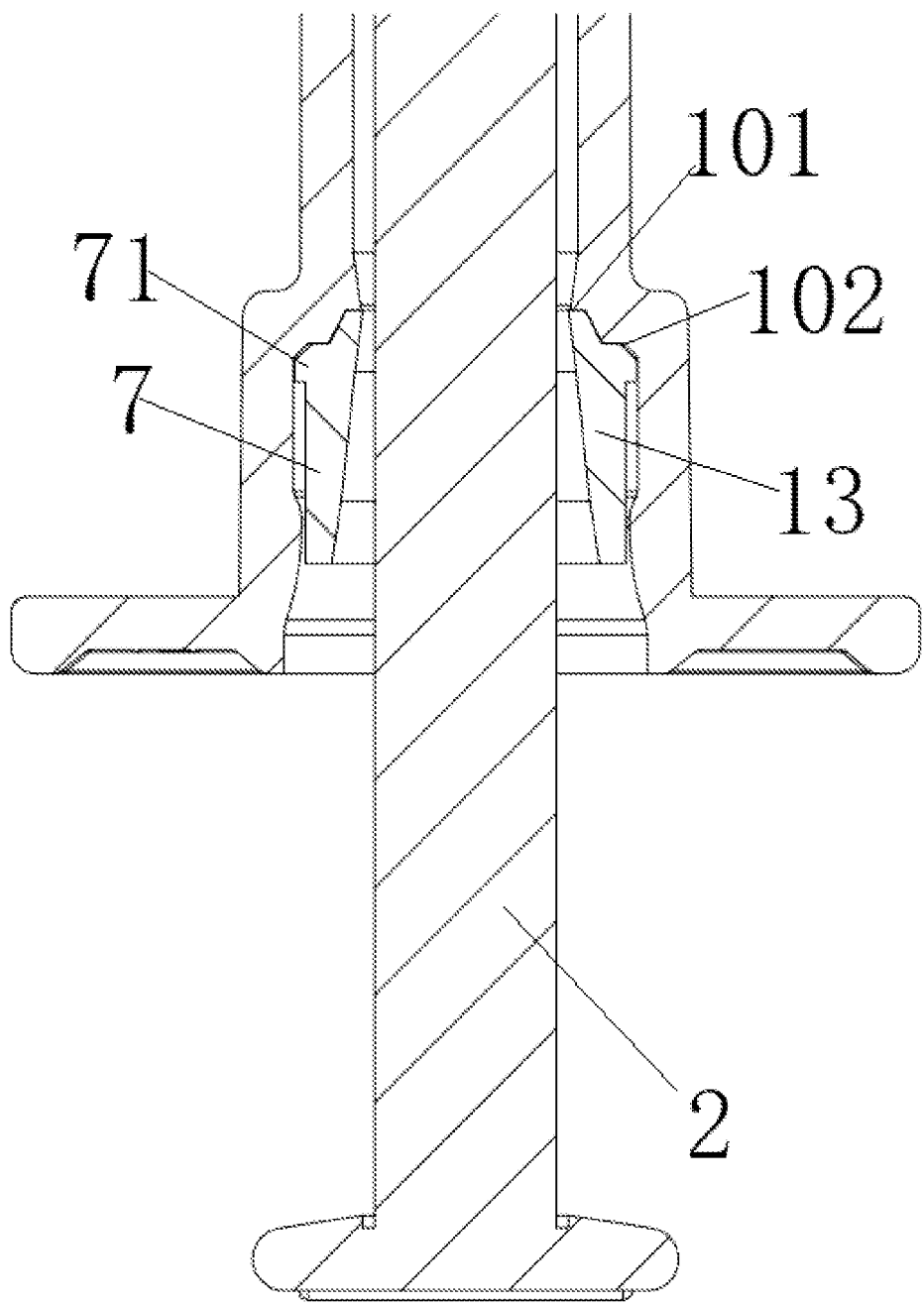
FIG. 7b is a schematic diagram of a status of the clamp and the proximal end of the core rod when the safety syringe in FIG. 1 is not yet used for injection.

Further preferably, as shown in FIG. 2, FIG. 5 and FIG. 7b, the safety syringe further comprises a clamp 7 sleeved on an exterior of the core rod 2 and arranged in the position-limiting chamber 13; an annular boss 71 is provided on an outer wall of the clamp 7, and an outer circumferential wall of the annular boss 71 is fitted on an inner wall of the position-limiting chamber 13; the outer diameter of the elastic position-limiting ring 6 in its free state is larger than the inner diameter of the clamp 7 and smaller than the outer diameter of the annular boss 71.

Figure 9:
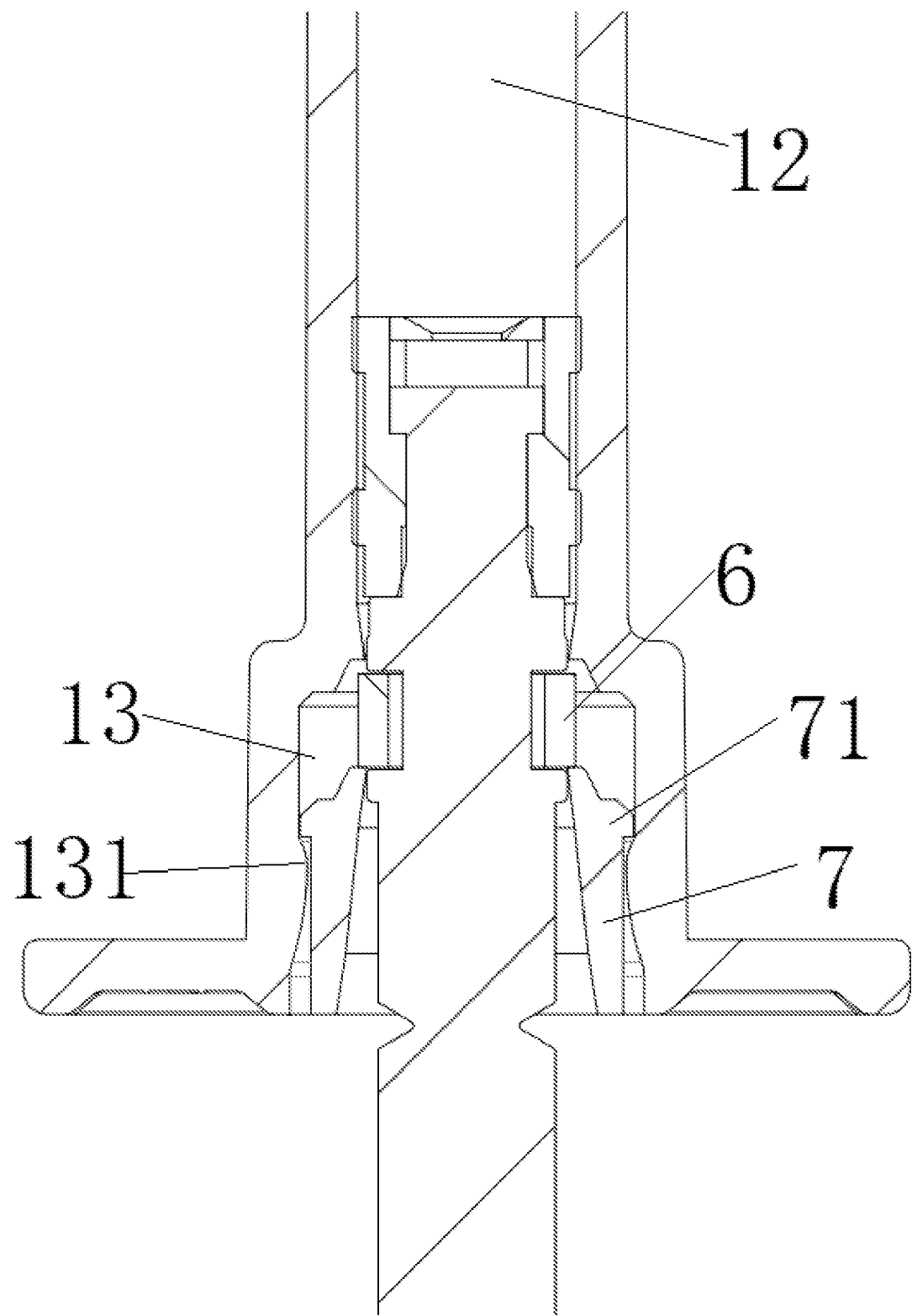
FIG. 9 is a schematic diagram of a status of the proximal end of the core rod and the proximal end of the needle sleeve when the safety syringe in FIG. 1 has completed injection and the core rod has been retracted.

In the retraction process of the core rod 2, the elastic position-limiting ring 6 moves together with the core rod 2 to gradually enter the position-limiting chamber 13, and after that, the elastic position-limiting ring 6 restores its position, the elastic position-limiting ring 6 sleeves onto the clamp 7, with the proximal end of the elastic position-limiting ring 6 abutting against the annular boss 71; and as the core rod 2 continues to slide in retraction, the elastic position-limiting ring 6 pushes the annular boss 71 to bring the entire clamp 7 to move towards the position-limiting protrusion 131, until the annular boss 71 abuts against the position-limiting protrusion 131, and correspondingly the distal end face of the elastic position-limiting ring 6 is constrained in the position-limiting chamber by the proximal end of the second stepped structure 10, or directly abuts against the proximal end face of the second stepped structure, as shown in FIG. 9, thereby realizing position-limiting against the sliding of the core rod 2.

In this embodiment, by the arrangement of the clamp 7, in one aspect, the clamp 7 cooperates with the elastic position-limiting ring 6 and the position-limiting protrusion 131 to limit the sliding of the core rod 2; in another aspect, the outer wall of the annular boss 71 on the clamp 7 fits on the inner wall of the position-limiting chamber 13, and a slidable sealed connection is formed between the two.

Further preferably, as shown in FIG. 6b and FIG. 6c, the afore-mentioned second stepped structure 10 comprises a third step 101 and a fourth step 102 in a ladder-shaped arrangement from the distal side to the proximal side; in the injecting state, a distal end surface of the afore-mentioned clamp 7 abuts against a step surface of the third step 101, and the annular boss 71 abuts against a step surface of the fourth step 102, so it is ensured that, in the injecting state, the clamp 7 and its annular boss 71 form a closely abutting sealed connection with the second stepped structure 10; in the retracting state, the distal end of the elastic position-limiting ring 6 is able to abut against the step surface of the third step 101.

Preferably, in FIG. 6c, the position-limiting protrusion 131 is in the form of a third position-limiting slope inclined radially from an outer side to an inner side.

As for the structure of the clamp 7, as shown in FIG. 5 and FIG. 7b, the diameter of an inner bore of the clamp 7 gradually decreases from the proximal side to the distal side, thereby forming a second throat segment, an inner diameter at the distal end of the second throat segment is equal to or slightly larger than the outer diameter of the core rod 2, which facilitates sliding of the core rod 2 in the inner bore of the clamp 7. An outer wall at the distal end of the clamp 7 is in the form of a first conical surface 72 with an outer diameter thereof gradually decreasing from the proximal side to the distal side, and the outer wall at the distal end of the annular boss 71 is also in the form of a second conical surface 73 with an outer diameter thereof gradually decreasing from the proximal side to the distal side; and correspondingly, as shown in FIG. 6c, the axial wall of the third step 101 is in the form of a third conical surface 101a that matches the first conical surface 72, and the axial wall of the fourth step 102 is in the form of a fourth conical surface 102b that matches the second conical surface 73. In the injecting state, the first conical surface 72 of the clamp 7 and the second conical surface 73 of the annular boss 71 are respectively fitted on the third conical surface of the third step 101 and the fourth conical surface of the fourth step 102.

Further preferably, an annular V-shaped groove is provided on an outer wall of the core rod 2, and a breakable site 23 is formed at a groove bottom of the V-shaped groove, as shown in FIG. 4, a handle part is provided at the proximal end of the core rod 2, and the breakable site 23 is located between the afore-mentioned elastic position-limiting ring 6 and the handle part. After the core rod 2 slides in retraction to bring the elastic position-limiting ring 6 into the position-limiting chamber 13, the elastic position-limiting ring 6 cooperates with the clamp 7 to lock the core rod 2 in the position-limiting chamber 13, and at this time, only an acting force applied on the proximal end of the core rod 2 is needed to break the core rod and completely destroy the safety syringe. The afore-mentioned breakable site 23 enables the core rod 2 to be more easily broken when a force is applied.

Moreover, it needs to be noted that, the afore-mentioned injecting state refers to the entire injecting process from the injection staring position to the injection finishing position, and also includes the injection staring position and the injection finishing position; the afore-mentioned retracting state refers to the entire retracting process from the retraction staring position to the retraction finishing position, after completion of the injection, and also includes the retraction staring position and the retraction finishing position.

The procedure of use of the safety syringe of this embodiment is as follows:

When the safety syringe has sucked fluid therein and an injection is needed, the core rod 2 is pushed towards the top end of the needle sleeve 1 (i.e., slides towards the distal side), the second slanted surface 211 of the position-limiting clamp ring 21 abuts against the first slanted surface of each second claw 33, as shown in FIG. 7a, at this time, if the core rod 2 is pushed further, because the distal end face of the rubber plug 5 abuts on the step surface of the second step 92, the rubber plug 5 is pressed to deform along with the continuous pushing of the core rod 2, so the core rod 2, relative to the rubber plug 5, is pushed into the inner bore of the first step 91, and due to the characteristics of the first slanted surface and elastic material of the second claws 33, the second slanted surface 211 of the position-limiting clamp ring 21 continues to slide towards the top end of the needle sleeve 1 along the first slanted surface of each second claw 33 to force the second claws 33 and the legs 32 to deform inwards in the radial direction, until each second claws 33 passes over the second slanted surface 211 and gets into the first avoiding hole 212 so as to be hooked onto the side wall of the position-limiting clamp ring 21, therefore, only a very small force is required to realize the interlocking between the second claws 33 and the position-limiting clamp ring 21, as shown in FIG. 8, and correspondingly, the clamp 7 is kept in the state shown in FIG. 7b throughout this process; meanwhile, because the second claws 33 and the legs 32 is forced to contract towards the central axis, the first claws 34 are brought to slip out of the first groove 111, that is, to slip off the first position-limiting slope, so that the needle base 3 slips out from the needle base chamber 11. Herein, when the safety syringe has finished the injection, the distal end face of the position-limiting clamp ring 21 abuts on the step surface of the first step 91, and with the existence of the O-shaped ring, after the injection is finished, there is minimal residual amount of medical fluid inside the syringe.

After the injection is finished, as shown in FIG. 7b, the core rod 2 is pulled back (i.e., the core rod 2 slides towards the proximal side), because the position-limiting clamp ring 21 is interlocked with the second claws 33, the core rod 2 would pull the needle base 3 and the needle tube 4 back into the transition chamber 12 of the needle sleeve 1. When the core rod 2 is pulled to a position near the bottom of the needle sleeve 1, due to the existence of the first throat segment (i.e., the second position-limiting slope) and the fact that the outer diameter of the elastic position-limiting ring 6 in its free state is larger than the inner diameter of the first throat segment, the elastic position-limiting ring 6 is pressed to deform by a pressing force towards the central axis exerted by the second position-limiting slope, until the elastic position-limiting ring 6 passes over the second position-limiting slope, then, the proximal end of the elastic position-limiting ring 6 abuts against the distal end of the annular boss 71 of the clamp 7, and as the core rod 2 continues to move in retraction, the elastic position-limiting ring 6 pushes the clamp 7 to move downwards along the inner chamber wall of the position-limiting chamber 13.

When the downward movement of the core rod 2 reaches the bottom, the elastic position-limiting ring 6 pushes the clamp 7 to reach the bottom of the needle sleeve 1, as shown in FIG. 9, at this time, the downside of the annular boss 71 on the clamp 7 abuts on the position-limiting protrusion 131 (i.e., the third position-limiting slope) and becomes fixed, the upper end of the elastic position-limiting ring 6 is in contact with, or is not in contact with, the step surface of the third step 101 of the second stepped structure 10, and either way, the step surface of the third step 101 blocks the distal end of the elastic position-limiting ring within the position-limiting chamber, and the needle tube is correspondingly positioned in the transition chamber 12 of the needle sleeve 1. From then on, the whole core rod 2 and the needle base 3 thereon is locked at the bottom of the needle sleeve 1 and cannot move again, and finally, the core rod 2 is snapped broken, so as to complete the self-destruction of the syringe.

The safety syringe of this embodiment can allow the safety syringe to self-destruct completely, which has high safety performance, a simplified structure, low cost, and is easy to manufacture, so that the production efficiency is increased. After the safety syringe finished the injection operation, the needle base 3 and the needle tube 4 of the syringe is completely fixed within the needle sleeve 1 of the syringe, thereby preventing any potential safety hazard caused by operation mistake or the needle sleeve 1 being too thin. The core rod 2 has a short stroke in retraction, so only very little feeling of pain is caused to the patient; the simplified structure is applicable to small-dosage syringes of 1 ml, 3 ml and so on, and is especially applicable to a vaccine syringe; because of the structure of the needle base 3 integrated with the second claws 33 and the first claws 34 in one piece, the difficulty level and cost for production manufacturing is greatly reduced, the production efficiency is increased, and the self-destruction operation of the syringe is also convenient with strong safety performance, so that the risk of an injury accident happening to the safety syringe is greatly reduced.

Embodiment 2

The present embodiment provides a safety syringe, and as compared to the safety syringe provided in Embodiment 1, its differences are as follows:

The positions of the second claws 33 and the position-limiting clamp ring 21 are interchanged, that is, the second claws 33 are provided on the distal end of the core rod 2, and the position-limiting clamp ring 21 is provided on the proximal end of the needle base 3. Likewise, in the injecting process of the core rod 2 sliding towards the distal side, the first slanted surface of each second claw 33 slides along the second slanted surface 211 of the position-limiting clamp ring 21, so as to cause the second claws 33 to contract and deform in the radial direction and slide into the inner bore of the position-limiting clamp ring 21, then, after the first slanted surface becomes separated from the second slanted surface 211, the second claws 33 restore their position in the radial direction, and thus the second claws 33 become hooked onto the distal end of the position-limiting clamp ring 21.

An alternative to the safety syringes of Embodiment 1 and Embodiment 2 is described below, while the second claws 33 in the above Embodiment 1 and Embodiment 2 contract in the radial direction under the action of the second slanted surface 211 or the first slanted surface so as to slide into the inner bore of the position-limiting clamp ring 21, and then, the second claws 33 restore their position in the radial direction so as to become hooked onto the position-limiting clamp ring 21 from the inner side of the inner bore of the position-limiting clamp ring to the outer side thereof.

However, in this alternative embodiment, the second claws 33 do not become hooked onto the position-limiting clamp ring 21 from the inner bore of the position-limiting clamp ring 21, but instead become hooked onto the position-limiting clamp ring 21 from the outer side of the position-limiting clamp ring 21. Specifically, the incline direction of the first slanted surface and the second slanted surface is opposite to the incline direction in Embodiment 1, that is, in the radial direction of the needle sleeve 1 in FIG. 4 and FIG. 3, both the first slanted surface 331 and the second slanted surface 211 incline upwards from an outer side to an inner side. When the second claws 33 slide along the second slanted surface 211 or when the first slanted surface slide on the position-limiting clamp ring 21, the second claws 33 expand outwards in the radial direction under the action of the slanted surface, so that the distance between the two second claws 33 increases, and the second claws 33 pass over the position-limiting clamp ring 21 along an outer surface thereof, and then, the second claws 33 restore their position in the radial direction so as to become hooked onto the position-limiting clamp ring 21 from the outer side to the inner side in the radial direction; correspondingly, the first groove is provided with the afore-mentioned first position-limiting slope 111b, and during the retraction process, the core rod slides to exert a pulling force on the needle base, so as to bring the first claws to slip out of the first groove along the first position-limiting slope.

Furthermore, as alternatives to the position-limiting clamp ring 21, other position-limiting members may also be used. For example, the position-limiting member is a circular disk, and the distal end of the core rod 2 is fixed on the proximal end of the circular disk; or, the circular disk is fixed on the proximal end of the needle base 3, and it is only required that, in the injection process of the core rod 2 sliding towards the distal side, the second claws 33 expand in the radial direction under the abutting force of a slanted surface to pass over the outer side of the circular disk so as to embrace the circular disk, thereby realizing the interlocking between the second claws 33 and the position-limiting member.

Apparently, the afore-mentioned embodiments are merely examples illustrated for giving a clear description, rather than limiting the implementation ways thereof. For a person with ordinary skill in the art, various changes and modifications in other different forms can be made on the basis of the afore-mentioned description. It is unnecessary and impossible to exhaustively list all the implementation ways herein. However, any obvious changes or modifications derived from the afore-mentioned description are intended to be embraced within the protection scope of the present application.

The invention claimed is:

1. A safety syringe, comprising
a needle sleeve, with a first groove provided on an inner wall thereof,
a needle base, with at least two first claws provided on an outer wall thereof, the first claws being configured to clamp in the first groove; and
a core rod, sealedly and slidably arranged in the needle sleeve;
wherein:
one of a proximal end of the needle base and a distal end of the core rod is provided with at least two second claws, and the other one is provided with a position-limiting member;
the second claws are configured to abut against the position-limiting member along a slanted surface;
in an injecting state, when the core rod slides towards a distal side, the second claws are forced to slide along the slanted surface and deform in a radial direction of the needle sleeve under the action of the slanted surface, so as to pass over the position-limiting member and become hooked onto the position-limiting member;
in the injecting state or a retracting state, the core rod slides to drive the first claws to slip out of the first groove;
a mounting cavity of the needle sleeve comprises a needle base chamber and a transition chamber communicated with the needle base chamber;
the mounting cavity further comprises a position-limiting chamber communicated with a proximal end of the transition chamber;
the position-limiting chamber has an inner diameter larger than that of the transition chamber, and a second stepped structure is formed between the transition chamber and the position-limiting chamber;
the safety syringe further comprises an elastic position-limiting ring fixed on an outer wall of the core rod; a position-limiting protrusion is provided on an inner wall of the position-limiting chamber; an outer diameter of the elastic position-limiting ring in a free state is at least larger than an inner diameter of a proximal end of the transition chamber, and is also larger than an inner diameter of the position-limiting protrusion; and
in the retracting state, a distal end of the elastic position-limiting ring is constrained in the position-limiting chamber by a proximal end face of the second stepped structure, and a proximal end of the elastic position-limiting ring abuts against the position-limiting protrusion.

2. The safety syringe according to claim 1, wherein,
the second claws are arranged on the needle base or the core rod to protrude outwards; the position-limiting member is a position-limiting clamp ring;
in the injecting state, the second claws contract in the radial direction of the needle sleeve under the action of the slanted surface to slide into an inner bore of the position-limiting clamp ring, so as to pass over the position-limiting clamp ring and become hooked onto the position-limiting clamp ring.

3. The safety syringe according to claim 2, wherein,
at least one first avoiding hole is provided in a side wall of the position-limiting clamp ring;
in the injecting state, each of the second claws extends into a corresponding first avoiding hole in a one-to-one manner, so as to be hooked onto the side wall of the position-limiting clamp ring.

4. The safety syringe according to claim 2, wherein,
the second claws are provided on the proximal end of the needle base, the position-limiting clamp ring is provided on the distal end of the core rod; the needle base comprises
a ring-shaped body, with an outer wall of the ring-shaped body being sealedly arranged on an inner wall of the needle sleeve, and an inner bore of the ring-shaped body being configured for mounting a needle tube;
at least two legs, evenly distributed on a same circle, with a distal end of each of the legs being fixed on a proximal end surface of the ring-shaped body;
wherein, the first claws and the second claws are fixed on and protrude from outer walls of the legs in a one-to-one manner, and each of the first claws is arranged between the ring-shaped body and a corresponding second claw;
in the injecting state, the second claws slide along the slanted surface to drive the legs to swing inwards in the radial direction of the needle sleeve, so as to bring the first claws out of the first groove.

5. The safety syringe according to claim 4, wherein,
at least three legs are provided, and all of the legs are evenly distributed on a same circle; and
at least three first claws and at least three second claws are provided.

6. The safety syringe according to claim 1, wherein, a groove wall at a proximal side of the first groove is in the form of a first position-limiting slope that is inclined from a groove mouth to a groove bottom.

7. The safety syringe according to claim 4, wherein,
the transition chamber has an inner diameter larger than that of the needle base chamber, and a first stepped structure is formed between the needle base chamber and the transition chamber; and
the needle base is arranged in the needle base chamber, with the legs passing through an inner bore of the first stepped structure, so that the second claws extend into the transition chamber.

8. The safety syringe according to claim 7, wherein,
a rubber plug is sleeved on an exterior of the core rod, and the core rod is slidably and sealedly arranged in the transition chamber by means of the rubber plug.

9. The safety syringe according to claim 8, wherein,
a proximal end of the rubber plug is fixed on the core rod, and under the action of a pressing force generated by the core rod sliding towards the distal side, a distal end of the rubber plug is closely pressed against a proximal end surface of the first stepped structure;
at least one ring-shaped sealing protrusion is provided on an outer wall of the rubber plug, and the sealing protrusion along with the core rod is slidably and sealedly fitted on an inner wall of the transition chamber.

10. The safety syringe according to claim 9, wherein,
the first stepped structure comprises a first step and a second step in a ladder-shaped arrangement from the distal side to the proximal side;
in the injecting state, a distal end surface of the position-limiting clamp ring abuts against a step surface of the first step, and a distal surface of the rubber plug abuts against a step surface of the second step.

11. The safety syringe according to claim 1, wherein, a gap is provided in a circumferential wall of the elastic position-limiting ring.

12. The safety syringe according to claim 1, further comprising a clamp sleeved on an exterior of the core rod and arranged in the position-limiting chamber;
an annular boss is provided on an outer wall of the clamp, and an outer circumferential wall of the annular boss is fitted on an inner wall of the position-limiting chamber;
in the retracting state, the elastic position-limiting ring is driven by the sliding of the core rod such that the proximal end of the elastic position-limiting ring abuts against the annular boss to push the clamp to move towards the position-limiting protrusion until the clamp abuts against the position-limiting protrusion.

13. The safety syringe according to claim 12, wherein,
the second stepped structure comprises a third step and a fourth step in a ladder-shaped arrangement from the distal side to the proximal side;
in the injecting state, a distal end surface of the clamp abuts against a step surface of the third step, and the annular boss abuts against a step surface of the fourth step; in the retracting state, the distal end of the elastic position-limiting ring is able to abut against the step surface of the third step.

14. The safety syringe according to claim 1, characterized in that, the transition chamber comprises a straight cylindrical segment and a first throat segment fixed on a proximal end of the straight cylindrical segment, the first throat segment has an inner diameter that gradually decreases in a direction from the distal side to the proximal side;
the outer diameter of the elastic position-limiting ring in the free state is larger than the inner diameter of the first throat segment, and is smaller than or equal to an inner diameter of the straight cylindrical segment.

15. The safety syringe according to claim 1, characterized in that, an annular groove is provided on an outer wall of the core rod, and a breakable site is formed at a groove bottom of the annular groove.

* * * * *